United States Patent
Lee et al.

(10) Patent No.: US 10,835,464 B2
(45) Date of Patent: Nov. 17, 2020

(54) SUNSCREEN COMPOSITION CONTAINING SURFACE MODIFIED CERIUM OXIDE PARTICLES

(71) Applicant: SOULBRAIN CO., LTD., Seongnam-si (KR)

(72) Inventors: SeungHyun Lee, Seongnam-si (KR); Seok Joo Kim, Seongnam-si (KR)

(*) Notice: Subject to any disclaimer, the term of this patent is extended or adjusted under 35 U.S.C. 154(b) by 0 days.

(21) Appl. No.: 16/172,862

(22) Filed: Oct. 29, 2018

(65) Prior Publication Data

US 2019/0125639 A1    May 2, 2019

(30) Foreign Application Priority Data

Oct. 30, 2017 (KR) .................. 10-2017-0142617

(51) Int. Cl.
| | | |
|---|---|---|
| *A61K 8/29* | (2006.01) | |
| *A61K 8/27* | (2006.01) | |
| *A61Q 17/04* | (2006.01) | |
| *A61K 8/36* | (2006.01) | |
| *A61K 8/19* | (2006.01) | |
| *A61K 8/02* | (2006.01) | |

(52) U.S. Cl.
CPC .............. *A61K 8/29* (2013.01); *A61K 8/0241* (2013.01); *A61K 8/19* (2013.01); *A61K 8/27* (2013.01); *A61K 8/361* (2013.01); *A61Q 17/04* (2013.01); *A61K 2800/412* (2013.01); *A61K 2800/413* (2013.01); *A61K 2800/612* (2013.01)

(58) Field of Classification Search
None
See application file for complete search history.

(56) References Cited

U.S. PATENT DOCUMENTS

| | | | | |
|---|---|---|---|---|
| 6,482,441 B1 * | 11/2002 | Hasegawa | ................. | A61K 8/11 |
| | | | | 424/490 |
| 2007/0092423 A1 * | 4/2007 | Hyeon | ................. | B82Y 30/00 |
| | | | | 423/263 |
| 2007/0253989 A1 * | 11/2007 | Abe | ................. | A61K 8/11 |
| | | | | 424/401 |

* cited by examiner

*Primary Examiner* — Nannette Holloman
(74) *Attorney, Agent, or Firm* — Jongkook Park

(57) ABSTRACT

The present invention provides a sunscreen composition comprising cerium oxide ($CeO_2$) particles surface-modified with a saturated fatty acid having 10 to 30 carbon atoms or an unsaturated fatty acid having 10 to 30 carbon atoms. Since the sunscreen composition according to an embodiment of the present invention exhibits a high kinematic viscosity in the low-frequency region and high-frequency region, the formulation has excellent emulsification/dispersion phase stability and excellent spreadability, and thus the sunscreen composition can be effectively used as a cosmetic composition for blocking ultraviolet rays.

8 Claims, 2 Drawing Sheets

SUNSCREEN COMPOSITION CONTAINING SURFACE MODIFIED CERIUM OXIDE PARTICLES

CROSS-REFERENCE TO RELATED APPLICATIONS

This application claims priority under 35 U.S.C. § 119 to Korean Patent Application No. 10-2017-0142617, filed on Oct. 30, 2017, in the Korean Intellectual Property Office, the disclosure of which is incorporated herein by reference in its entirety.

TECHNICAL FIELD

The following disclosure relates to a sunscreen composition containing cerium oxide particles that are surface-modified with a fatty acid.

BACKGROUND

Since cosmetics containing sunscreen were developed for the first time in the United States in 1928, demand for sunscreens has been steadily increasing. Sunscreen aims to n prevent skin cancer, sunburn, sunlight aging, and the like, caused by ultraviolet rays. Recently, there is an increased interest in preventing sunlight aging through blocking of the ultraviolet rays corresponding to UVA1 and UVA2 wavelengths for the purpose of beauty. In addition to sunscreen, UV protection function is also added to most formulations such as BB cream, CC cream, sun cushion, sun spray, sun sticks, and the like.

In order to block ultraviolet rays, sunscreen is added to the formulations, and the added sunscreen can be divided into two types: organic sunscreens and inorganic sunscreens. Organic sunscreen is representatively a chemical sunscreen that converts light into heat, while inorganic sunscreen is representatively a physical sunscreen that reflects, scatters, and absorbs light. Unlike basic cosmetics, sunscreen is mainly used to attenuate ultraviolet rays at an upper part of the epidermis, i.e., at the outermost part of the skin. However, organic sunscreens such as avobenzone are likely to penetrate the skin due to their small molecular size. Organic sunscreen has advantages of low white cast and a wide range of absorption wavelengths, but has disadvantages of causing skin trouble or side effects such as a burning sensation in the eyes when applied to areas near the eyes in the case of having a sensitivity. Meanwhile, inorganic sunscreen is relatively advantageous in safety and has good sun protection power, but problems such as white cast may occur since it is a white pigment having a high refractive index. Due to the nature-friendly trend of cosmetic materials in recent years, in Korea, there has been a high preference for UV protection products in the category of 'inorganic sunscreen' formulations which are composed of only an inorganic sunscreen as a functional component.

Titanium dioxide ($Tio_2$) and zinc oxide (ZnO) are used as inorganic sunscreens, but there are various disadvantages to their use. First, the energy bandgaps of titanium dioxide and zinc oxide are 3.0 eV and 3.2 eV, respectively, which are advantageous for absorption of UVB and UVA2, and thus it is not possible to absorb UVA1, the intermediate wavelength, with titanium dioxide and zinc oxide alone. Second, the refraction indexes of titanium dioxide and zinc oxide are high at 2.7 and 2.2, respectively, and thus a white cast phenomenon in which white color appears when applied to the skin may appear prominently. Third, titanium dioxide and zinc oxide may cause component denaturation and pigmentation of the formulation due to their large photocatalytic power which decomposes or denatures organic material, especially pigment, when exposed to light energy. In particular, when the photocatalytic power is large, it is necessary for a surface to be covered with a second material for safety reasons. In the case of titanium dioxide, the surface is covered with aluminum oxide ($Al_2O_3$) or silicon dioxide ($SiO_2$) up to at an amount of 20 parts per weight or more. However, when the surface is covered with aluminum oxide and silicon dioxide, there are disadvantages in that the powder texture is heavy, and the composition is not softly applied, thus resulting in a hard and dry feeling of use. Accordingly, there is a need to develop a sunscreen composition capable of compensating for the above-described disadvantages.

Therefore, the present inventors studied sunscreen and found that when cerium oxide was surface-modified with a fatty acid and used as a sunscreen composition, it was possible to form a UV sunscreen composition capable absorbing UVA1, suppressing a white cast due to a low refractive index, and being stable due to low photocatalytic power, and completed the present invention.

SUMMARY

An embodiment of the present invention is directed to providing a sunscreen composition.

In addition, an embodiment of the present invention is directed to providing a method of preparing a sunscreen composition.

DETAILED DESCRIPTION OF EMBODIMENTS

Figure 1:
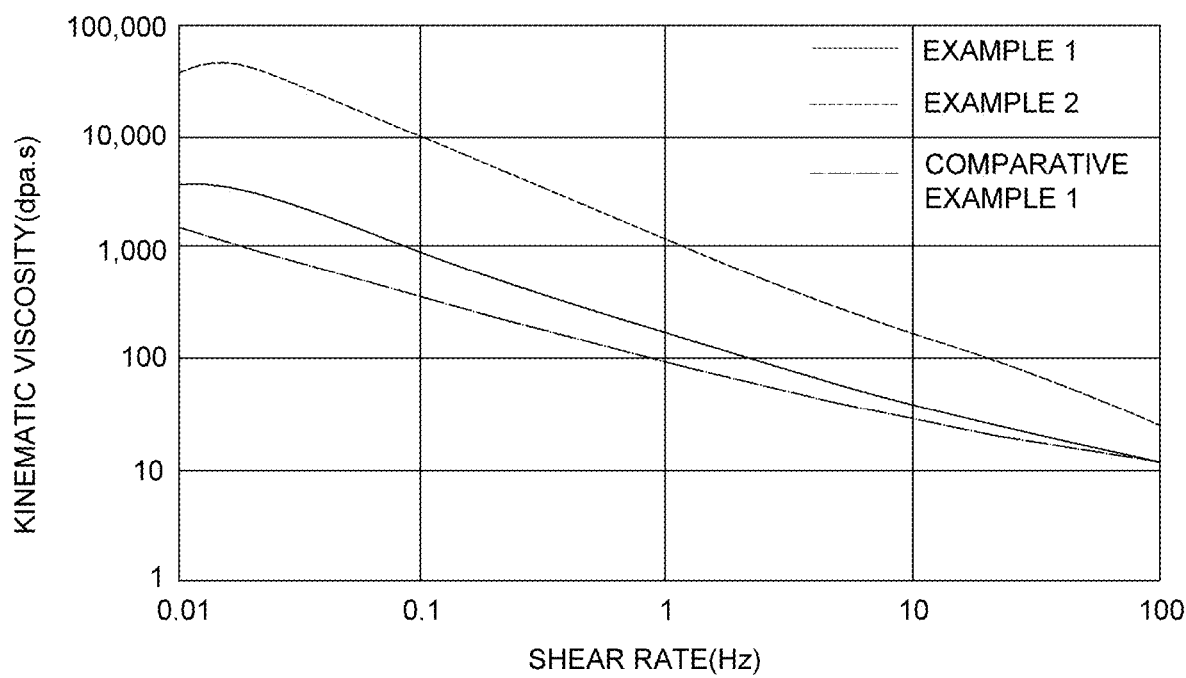
FIG. 1 is a graph showing results of the measured kinematic viscosities of Examples 1 and 2 and Comparative Example 1.

Hereinafter, a detailed description of the present invention is provided. It should be understood, however, that the following description is an example only, and the present invention is only limited by the scope of the following claims.

In addition, the terms used in the invention are only used to describe certain embodiments, and they are not intended to limit the scope of the invention. The expression of singular or plural words is only made in context of grammar, and can include both meanings. Unless specifically stated otherwise, expressions such as "including" or "comprising" do not indicate the exclusion of all other components, and additional components may also be included.

An aspect of the present invention provides a sunscreen composition comprising cerium oxide ($CeO_2$) particles surface-modified with a saturated fatty acid having 10 to 30 carbon atoms or an unsaturated fatty acid having 10 to 30 carbon atoms.

Here, the cerium oxide particles may be produced from a cerium precursor such as cerium hydroxide, cerium carbonate, cerium nitrate, cerium chloride, ammonium cerium nitrate, or the like. Any cerium oxide particles produced by a conventional method for producing cerium oxide may be used without any particular limitation.

In addition, the cerium oxide particles may have a plate shape, a flake shape, a spherical shape, or the like, and there is no particular limitation on the shape of the cerium oxide particles.

Further, the cerium oxide ($CeO_2$) particles may have a primary particle size of 3 to 35 nm, 5 to 32 nm, and preferably 10 to 30 nm, and may have a secondary particle size of 50 to 600 nm, 80 to 550 nm, and preferably 100 to 500 nm. The ratio of the secondary particle size to the primary particle size may be 1 to 55, 3 to 53, and preferably 5 to 50.

The cerium oxide particles may be included in the ultraviolet screening composition according to the present invention to absorb a wavelength of the UVA1 region, which is a mid-wavelength region of ultraviolet rays, thus resulting in widening of the ultraviolet blocking absorption region of the sunscreen composition.

In addition, the saturated fatty acid having 10 to 30 carbon atoms may be capric acid, undecylic acid, lauric acid, tridecylic acid, myristic acid, palmitic acid, margaric acid, stearic acid, nonadecylic acid, arachidic acid, heneicosanoic acid, behenic acid, tricosanoic acid, lignoceric acid, pentacosanoic acid, cerotic acid, heptacosanoic acid, montanic acid, nonacosanoic acid or melissic acid.

Further, the unsaturated fatty acid having 10 to 30 carbon atoms may have a ratio of the number of double bonds to carbon atom number of 18:1 to 18:3. Specifically, the unsaturated fatty acid having 10 to 30 carbon atoms may be α-linolenic acid, linoleic acid, γ-linolenic acid, dihomo-γ-linolenic acid, palmitoleic acid, vaccenic acid, oleic acid or trans-elaidic acid.

The saturated fatty acid having 10 to 30 carbon atoms and the unsaturated fatty acid having 10 to 30 carbon atoms are not limited to the above-described types and includes=both saturated and unsaturated fatty acids having a hydrocarbon ring having 10 to 30 carbon atoms.

The sunscreen composition according to the present invention has excellent emulsification/dispersion phase stability and excellent spreadability through the surface-modification of the cerium oxide particles with a fatty acid having a specific length of 10 to 30 carbon atoms. When the surface-modification is performed with a fatty acid having 10 to 30 carbon atoms, the formulation can have excellent dispersion stability since emulsification can be smoothly performed.

When the number of carbon atoms is less than 10, association of an oil phase may not be sufficient due to absence of lipophilic property, and when the number of carbon atoms exceeds 30, when cosmetic ingredients are prepared and applied to skin, a feeling of excessive oiliness may occur, which may hinder the feeling of use.

In the sunscreen composition according to the present invention, the content of the saturated fatty acid or the unsaturated fatty acid may be 0.3 to 15 wt %, 0.5 to 11 wt %, and more preferably 1 to 10 wt %, based on the surface-modified cerium oxide ($CeO_2$) particles.

When surface-modifying the cerium oxide particles with a content of saturated fatty acid or unsaturated fatty acid that is less than 0.3 wt %, all of the cerium oxide particles may not be surface-modified, thus causing problems in emulsification/dispersion at the time of preparing a solvent. Further, when surface-modifying the cerium oxide particles with a content of saturated fatty acid or unsaturated fatty acid exceeding 15 wt % based on the solid content, excess fatty acid molecules remaining after covering the particle surfaces may become scattered and attached to each other, and may then act as impurities at the time of preparation of cosmetic ingredients. Further, when the content of the fatty acid is excessively small, the particle surface cannot be sufficiently coated, and when the content of the fatty acid is excessively large, the excess fatty acid molecules may be scattered and attached to each other and may act as impurities in the preparation of cosmetic ingredients, which may thus cause rancidity of the cosmetic ingredients and hinder the feeling of use due to an excessive oily feeling.

In the sunscreen composition according to the present invention, the cerium oxide particles are surface-modified with a fatty acid, thereby allowing the cerium oxide particles, which are hydrophobic, to have excellent emulsification/dispersion phase stability.

The content of the surface-modified cerium oxide particles may be 1 to 50 wt %, 2 to 40 wt %, and preferably 5 to 20 wt %, based on the total sunscreen composition.

When the content of the surface-modified cerium oxide particles is less than 1 wt %, the wavelength of the UVA1 region cannot be absorbed due to excessively small content of the cerium oxide particles. When the content of the surface-modified cerium oxide particles exceeds 50 wt %, viscosity of the cosmetic ingredients increases excessively due to the excessively high solid content, which may hinder the spreadability. In addition, when the content of the surface-modified cerium oxide particles is less than 1 wt %, it may be difficult to expect any ultraviolet blocking effect.

Further, the sunscreen composition may further comprise one or more particles selected from the group consisting of titanium oxide particles and zinc oxide particles.

Here, the content of the titanium oxide may be 1 to 25 wt %, 2 to 23 wt %, and preferably 5 to 20 wt %, based on the total sunscreen composition. The content of the zinc oxide particles may be 1 to 25 wt %, 2 to 23 wt %, and preferably 5 to 20 wt %, based on the total sunscreen composition. Here, the content of the titanium oxide and zinc oxide is not limited if it is a content which does not hinder the effects of the present invention.

The sunscreen composition may further comprise silicone oil, fibrous agents, emulsifiers, moisturizers, plasticizers, and purified water.

Here, the organic solvent may be alcohol, glycol, silicone oil, natural oil, vegetable oil, nut oil, mineral oil, or the like. The organic solvent serves as a solvent for dispersing the cerium oxide particles surface-modified with the fatty acid. In addition, the organic solvent may be any organic solvent without particular limitation as long as it is an organic solvent capable of dispersing cerium oxide particles surface-modified with fatty acid and being suitable for preparing a cosmetic composition in a formulation with good spreadability.

As the silicone oil, dimethicone, cetyl dimethicone, cyclopentasiloxane, cyclohexasiloxane or stearyl dimethicone may be used. The silicone oil may serve to form an oil phase in emulsifying cosmetic ingredients and to improve the feeling of use.

As the fibrous agent, VGL silk, and the like may be used. The fibrous agent may serve to improve the feeling of use of the sunscreen composition.

As the emulsifier, PEG silicone emulsifier, non-ionic W/O emulsifier, positive-ionic emulsifier, negative-ionic emulsifier, and the like may be used. The emulsifier can emulsify each element of the sunscreen composition according to the present invention. Further, the emulsifier may serve to improve stability of the formulation by trapping the particles in emulsified particles of an oil phase.

The moisturizer may be polyols such as 1,2-hexanediol, glycerin, propylene glycol, butylene glycol, polyethylene glycol, sorbitol, trehalose, and the like; natural moisturizing factors (NMFs) such as amino acids, urea, lactate, PCA-Na, and the like; and polymeric moisturizers such as hyaluronate, chondroitin sulfate, hydrolyzed collagen, and the like. The moisturizer may increase the moisturizing power of the sunscreen composition according to the present invention and simultaneously act as a preservative.

The plasticizer may be dipropylene glycol (DPG), and the like.

In addition to the above-described components, the sunscreen composition according to the present invention may be appropriately blended with components that are mixed in general cosmetic compositions such as oil, wax, surfactants, thickeners, pigments, cosmetic additives, powders, saccharides, antioxidants, buffers, various extracts, stabilizers, preservatives, fragrances, and the like, within the range in which the effects of the present invention are not impaired.

Here, the oil may be vegetable oils such as evening primrose oil, rosehip oil, castor oil, olive oil, and the like, animal oils such as mink oil, squalane, and the like, mineral oils such as liquid paraffin, vaseline, and the like, or synthetic oils such as silicone oil, isopropyl myristate oil, and the like.

The wax may be a vegetable wax such as carnauba wax, candelilla wax, jojoba oil, and the like, or an animal wax such as beeswax, lanolin, and the like.

The surfactant may be an anionic surfactant, a cationic surfactant, an amphoteric surfactant, a non-ionic surfactant, and the like.

In addition, the thickener may be, for example, a water-soluble polymer.

Examples of the water-soluble polymer may include plant-based (polysaccharide-based) natural polymers such as guar gum, locust bean gum, quince seed, carrageenan, galactan, gum arabic, tragacanth gum, pectin, mannan, starch, and the like; microbial (polysaccharide-based) natural polymers such as xanthan gum, dextran, succinol glucan, curdlan, hyaluronic acid, and the like; animal-based (protein-based) natural polymers such as gelatin, casein, albumin, collagen, and the like; cellulose-based semisynthetic polymers such as methyl cellulose, ethyl cellulose, hydroxyethyl cellulose, hydroxypropyl cellulose, carboxymethyl cellulose, methylhydroxypropyl cellulose, and the like; starch-based semisynthetic polymers such as soluble starch, carboxymethyl starch, methyl starch, and the like; alginic acid-based semisynthetic polymers such as alginic acid propylene glycol ester, alginate, and the like; other polysaccharide-based derivative semisynthetic polymers; vinyl-based synthetic polymers such as polyvinyl alcohol, polyvinylpyrrolidone, polyvinylmethylether, carboxyvinyl polymer, sodium polyacrylate, and the like; other synthetic polymers such as polyethylene oxide, ethylene oxide, propylene oxide block copolymers, and the like; and inorganic materials such as bentonite, laponite, microdispersed silicon, colloidal alumina, and the like.

The pigment may be, for example, a synthetic pigment or a natural pigment, wherein the synthetic pigment may be: water-soluble/oil-soluble pigments such as FD&C Yellow No. 6, FD&C Red No. 4, and the like; inorganic pigments such as iron oxide, ultramarine, and the like; organic pigments such as D&C Red No. 30, D&C Red No. 36, and the like; and lakes such as FD&C Yellow No. 6 Al lake, and the like; and the natural pigment may be: carotenoid-based pigments such as β-carotene, β-apo-8-carotenal, rilopine, capsanthin, bixin, crocin, canthaxanthin, and the like; flavonoid-based pigments such as shisonin, lamanine, ninocyanine, carthamin, safrole yellow, rutin, quercetin, cocoa pigment, and the like; flavin-based pigments such as riboflavin, and the like, quinone-based pigments such as laccaic acid, carminic acid (cochineal), kermesic acid, alizaine, shikonin, alkannin, nikino chrome, and the like; porphyrin-based pigments such as chromophil, hemoglobin, and the like; diketone-based pigments such as curcumin (turmeric), or the like; and a betacyanine-based pigment such as betanine, and the like.

The cosmetic additive may be, for example, a vitamin, a plant extract, or an animal extract, wherein the vitamin may be retinol (vitamin A), tocopherol (vitamin E), ascorbic acid (vitamin X), and the like; the plant extract may be menthol (peppermint), azulene (chamomile), allantoin (wheat), caffeine (coffee), licorice extract, cinnamon extract, green tea extract, lavender extract, lemon extract, and the like; and the animal extract may be placenta (placenta of cattle), royal jelly (bee secretion), snail extract (mucus secretion), and the like.

Another aspect of the present invention provides a method for preparing a sunscreen composition, comprising: a step of adding and stirring cerium oxide into purified water to prepare a supernatant; a step of adding and stirring a saturated fatty acid having 10 to 30 carbon atoms or an unsaturated fatty acid having 10 to 30 carbon atoms into the supernatant; a step of drying the stirred solution to obtain cerium oxide particles surface-modified with the fatty acid; a step of dispersing the cerium oxide particles surface-modified with the fatty acid in an organic solvent; and a step of mixing the organic solvent with one or more substances selected from the group consisting of silicone oil, fibrous agents, emulsifiers, moisturizers, plasticizers, and purified water.

Hereinafter, the method for preparing a sunscreen composition is described in detail for each step.

The method for preparing a sunscreen composition according to the present invention comprises a method for producing cerium oxide particles surface-modified with a fatty acid, which comprises: a step of adding and stirring cerium oxide into purified water to prepare a supernatant; a step of adding and stirring a saturated fatty acid having 10 to 30 carbon atoms or an unsaturated fatty acid having 10 to 30 carbon atoms into the supernatant; and a step of drying the stirred solution to obtain cerium oxide particles surface-modified with the fatty acid.

First, the step of adding and stirring cerium oxide into purified water to prepare a supernatant is performed by adding cerium oxide particles to the purified water so as to disperse the cerium oxide particles, which is a process for preparing the cerium oxide in a solvent phase so that the fatty acid can be uniformly modified on the surface of the cerium oxide.

Here, the particle size of the cerium oxide used may be 0.01 to 1 μm, 0.05 to 0.5 μm, and preferably 0.08 to 0.2 μm. The amount of the purified water is preferably 2 to 10 times larger based on the weight of the cerium oxide.

Next, the step of adding and stirring a saturated fatty acid having 10 to 30 carbon atoms or an unsaturated fatty acid having 10 to 30 carbon atoms into the supernatant is performed in order to dissolve the fatty acid for surface-modifying the cerium oxide in the supernatant, and then to disperse the cerium oxide particles uniformly.

Here, the saturated fatty acid having 10 to 30 carbon atoms may be capric acid, undecylic acid, lauric acid, tridecylic acid, myristic acid, palmitic acid, margaric acid, stearic acid, nonadecylic acid, arachidic acid, heneicosanoic acid, behenic acid, tricosanoic acid, lignoceric acid, pentacosanoic acid, cerotic acid, heptacosanoic acid, montanic acid, nonacosanoic acid or melissic acid.

Further, the unsaturated fatty acid having 10 to 30 carbon atoms may have a ratio of the number of double bonds to carbon atom number of 18:1 to 18:3. Specifically, the unsaturated fatty acid having 10 to 30 carbon atoms may be α-linolenic acid, linoleic acid, γ-linolenic acid, dihomo-γ-linolenic acid, palmitoleic acid, vaccenic acid, oleic acid or trans-elaidic acid.

The saturated fatty acid having 10 to 30 carbon atoms and the unsaturated fatty acid having 10 to 30 carbon atoms are not limited to the above-described types, and include both saturated and unsaturated fatty acids having a hydrocarbon ring having 10 to 30 carbon atoms.

Here, the stirring temperature may be 20 to 50° C., and preferably 25 to 35° C.; the stirring time may be 10 to 180 minutes, and preferably 30 to 60 minutes; and the stirring speed may be 100 rpm to 2,000 rpm, and preferably 500 rpm to 1,000 rpm.

Next, the step of drying the stirred solution to obtain cerium oxide particles surface-modified with the fatty acid is performed in order to react the fatty acid in the solution with the surface-modified cerium oxide, thereby finally obtaining cerium oxide particles surface-modified with the fatty acid in a solid form.

Here, the method may further comprise removing impurities from the stirred solution before stirring. In order to remove the impurities, a centrifugal separator, or the like, may be used, and there is no particular limitation on the method for removing the impurities.

The drying temperature may be 30 to 120° C., 50 to 100° C., and more preferably 60 to 80° C., and the drying time may be 1 to 24 hours, 2 to 12 hours, and more preferably 3 to 6 hours.

Further, the method for preparing a sunscreen composition according to the present invention comprises: a step of dispersing the cerium oxide particles surface-modified with the fatty acid in an organic solvent after obtaining the cerium oxide particles surface-modified with the fatty acid as described above; and a step of mixing the organic solvent with one or more substances selected from the group consisting of silicone oil, fibrous agents, emulsifiers, moisturizers, plasticizers, and purified water.

First, the step of dispersing the cerium oxide particles surface-modified with the fatty acid in an organic solvent is performed in order to uniformly disperse the cerium oxide particles, which have an increased emulsification/dispersion ability due to the surface-modification, in an organic solvent. Here, the organic solvent is preferably an alcohol. The alcohol used may be ethyl alcohol, behenyl alcohol, phenethyl alcohol, glycol, derivatives thereof, and the like.

Next, the step of mixing the organic solvent with one or more substances selected from the group consisting of silicone oil, fibrous agents, emulsifiers, moisturizers, plasticizers, and purified water is performed in order to mix the cerium oxide particles dispersed in the organic solvent with various mixtures for preparing a cosmetic composition, thereby preparing a formulation that can be used as a cosmetic composition.

Here, types of the organic solvents, silicone oil, fibrous agents, emulsifiers, moisturizers, and plasticizers that may be used are the same as described above.

Hereinafter, the present invention is described in detail with reference to the following Examples and Experimental Examples.

However, the following Examples and Experimental Examples are just Examples, and thus they do not limit the scope of the present invention.

Production Example 1: Production 1 of Cerium Oxide Particles

Cerium oxide particles were produced to prepare the sunscreen compositions according to the present invention. Cerium hydroxide, cerium carbonate, cerium nitrate, cerium chloride, and ammonium cerium nitrate may be used individually or blended and mixed. Heat treatment was performed on cerium carbonate at 500 to 1200° C. for 12 hours to obtain cerium oxide particles.

Example 1: Preparation 1 of UV Sunscreen Composition According to Present Invention Cerium oxide particles surface-modified with stearic acid were used to prepare a sunscreen composition.

Step 1: Surface-Modification of Cerium Oxide

First, 5 g of cerium oxide having a particle size of 110 nm prepared in Preparation Example 1 was added to 150 g of purified water, followed by ultrasonic agitation for 24 hours to disperse the particles, after which the supernatant was recovered. Next, sodium stearate was dissolved in the supernatant at a molar ratio of 1:1.5, and the pH of the mixed solution was adjusted to 10.5 by adding 0.1N NaOH as an acidity regulator. High-speed stirring was then performed at 45° C. for 24 hours. After the stirring, the mixture was washed three times by centrifugation to remove sodium and residual impurities from the solution.

Finally, after formation of negative pressure with a vacuum oven, the resultant solution was dried by vacuum hot air at 50° C. for 24 hours to obtain a surface-modified cerium oxide solid.

Step 2: Preparation of Sunscreen Composition

A cerium oxide solution was prepared by dispersing 200 g of the surface-modified cerium oxide solid obtained in step 1 in 800 g of a mixed alcohol solvent containing glycol, behenyl alcohol, ethanol, and purified water at a ratio of 1:1:2:8 so as to have a content of 20 wt %. Then, the prepared solution (54.55 wt %), silicone oil (DC 245, 10 wt %), a fibrous agent (VGL silk, 10 wt %), a PEG silicone emulsifier (KF 6017, 3 wt %), a non-ionic W/O emulsifier (Abil em 90, 2.5 wt %), a moisturizer (1,2-hexanediol, 2 wt %), a plasticizer (DPG, 10 wt %), and purified water (7.95 wt %) were mixed to prepare a sunscreen composition.

Example 2: Preparation 2 of Sunscreen Composition According to Present Invention A sunscreen composition was prepared in the same manner and with the same composition as in Example 1, except that cerium oxide particles surface-modified with oleic acid instead of stearic acid were used.

Comparative Example 1: Preparation 1 of Sunscreen Composition

A sunscreen composition was prepared in the same manner and with the same composition as in Example 1, except that cerium oxide particles surface-modified with caproic acid instead of stearic acid were used.

Comparative Example 2: Preparation 2 of Sunscreen Composition

A sunscreen composition was prepared in the same manner and with the same composition as in Example 1, except that cerium oxide particles surface-modified with citric acid instead of stearic acid were used.

Comparative Example 3: Preparation 3 of Sunscreen Composition

The ultraviolet sunscreen composition was prepared using cerium oxide particles that were not surface-modified.

First, 144 g of solid cerium oxide was dispersed in 576 g of purified water so as to have the content of 20 wt %, thereby preparing a cerium oxide solution. The prepared solution (54.55 wt %), silicone oil (DC 245, 10 wt %), a fibrous agent (VGL silk, 10 wt %), a PEG silicone emulsifier (KF 6017, 3 wt %), a non-ionic W/O emulsifier (Abil em 90, 2.5 wt %), a moisturizer (1,2-hexanediol, 2 wt %), a plasticizer (DPG, 10 wt %), and purified water (7.95 wt %) were mixed to prepare a sunscreen composition.

Composition ratios of the sunscreen compositions prepared in Examples 1 and 2 and Comparative Examples 1, 2 and 3, and the types of compounds used for surface-modification are summarized in Table 1 below.

TABLE 1

| | Composition ratios (wt %) | | | | |
|---|---|---|---|---|---|
| Components | Example 1 | Example 2 | Comparative Example 1 | Comparative Example 2 | Comparative Example 3 |
| DC 245 | 10 | 10 | 10 | 10 | 10 |
| VGL silk | 10 | 10 | 10 | 10 | 10 |
| KF 6017 | 3 | 3 | 3 | 3 | 3 |
| Abil em 90 | 2.5 | 2.5 | 2.5 | 2.5 | 2.5 |
| 1,2-Hexanediol | 2 | 2 | 2 | 2 | 2 |
| Water | 7.95 | 7.95 | 7.95 | 7.95 | 7.95 |
| DPG | 10 | 10 | 10 | 10 | 10 |
| UV Blocking Agent | 54.44 | 54.44 | 54.44 | 54.44 | 54.44 |
| Total | 100 | 100 | 100 | 100 | 100 |
| Surface-Modification Compound | Stearic Acid | Oleic Acid | Caproic Acid | Citric Acid | — |
| Number of Carbon Atoms of Surface-Modification Compound | 18 | 18 | 6 | 6 | — |
| Number of Double Bonds of Surface-Modification Compound | 0 | 1 | 0 | 0 | — |

※: UV blocking agent: mixed solution of cerium oxide particles and organic solvent

Experimental Example 1: Measurement Experiment of Kinematic Viscosity

Kinematic viscosities of Examples 1 to 2 and Comparative Examples 1 to 3 were measured, compared, and analyzed.

The kinematic viscosity is a numerical value obtained by kinematically recording the viscosity at every moment where the shear rate frequency changes. Emulsification/dispersion phase stability of the formulation can be evaluated at a low frequency of 0.1 Hz or less, and the viscosity of the formulation can be measured at a high frequency of 10 Hz or more. It is also possible to evaluate the spreadability of the formulation through the slope of the kinematic viscosity versus the shear rate.

The kinematic viscosities of the UV sunscreen formulations of Example 1, Example 2, and Comparative Example 1 were measured using a Rheometer MCR302 manufactured by Anton Paar. The sunscreen formulations were applied on a rotating disk (R=1.25). Then, kinematic viscosities of the respective formulations were measured at shear rates from 0.001 to 100 Hz, and the results thereof are shown in FIG. 1 as a graph. The kinematic viscosity values at a low frequency (0.1 Hz) and a high frequency (100 Hz) are summarized in Table 2 below. Meanwhile, the formulations of Comparative Example 2 and Comparative Example 3 could not be emulsified, and thus the kinematic viscosities could not be measured.

TABLE 2

| | Low Frequency (0.1 Hz) | High Frequency (100 Hz) |
|---|---|---|
| Example 1 | 876 dPa · s | 12.1 dPa · s |
| Example 2 | 10,200 dPa · s | 26.4 dPa · s |
| Comparative Example 1 | 355 dPa · s | 12 dPa · s |
| Comparative Example 2 | Cannot be Emulsified | |
| Comparative Example 3 | Cannot be Emulsified | |

As can be seen from the above Table 2, Examples 1 and 2 exhibited relatively high kinematic viscosities in the low frequency region. In particular, in Example 2, since the kinematic viscosity was remarkably high at over 10,000 dPa·s, it can be seen that the formulation had excellent emulsification/dispersion phase stability. Further, in the high frequency region, it could be confirmed that Example 2 had a kinematic viscosity more than twice as high as that of Comparative Example 1, and it exhibited a high viscosity property, which indicates that Example 2 may be prepared into a cream formulation. In Comparative Example 1, it could be seen that in consideration of the kinematic viscosity in the low frequency region, the emulsification/dispersion phase was unstable, and phase separation, sedimentation, and precipitation were likely to occur sequentially over time.

FIG. 1 is a graph showing the results of the kinematic viscosity measurements of Examples 1 and 2, and Comparative Example 1, measured at shear rates from 0.001 to 100 Hz.

As can be seen from FIG. 1, the slopes of Examples 1 and 2 are higher than that of Comparative Example 1. This means that the spreadabilities of Examples 1 and 2 are relatively superior to that of Comparative Example 1, and indicates that the sunscreen compositions according to the present invention can be effectively used for cosmetic applications.

Figure 2:
FIG. 2 is an image showing the sunscreen formulations prepared in Examples 1 and 2 and Comparative Example 1.

FIG. 2 is an image showing the sunscreen formulations prepared in Examples 1 and 2, and Comparative Example 1.

As can be seen from FIG. 2, Example 1 and Example 2 have excellent stability of the formulation since no phase separation phenomenon occurred. On the other hand, it can be seen that in Comparative Example 1, the phase separation phenomenon appeared due to low emulsification/dispersion stability of the formulation. Accordingly, the sunscreen composition according to the present invention has secured stability of the formulation, thereby allowing effective use as a composition for producing cosmetics for blocking ultraviolet rays.

Experimental Example 2: Measurement Experiment of Ultraviolet Blocking Effect The sun protection factor (SPF) of each of the UV blocking formulations prepared in Examples 1 to 2 and Comparative Examples 1 to 3 was measured.

The SPF of each of the formulations of Example 1, Example 2, and Comparative Example 1 was measured six times using an SPF analyzer 290S manufactured by Laser Components, UK, and each average value was calculated and shown in Table 3 below. Meanwhile, the formulations of Comparative Example 2 and Comparative Example 3 could not be emulsified, and thus the SPFs could not be measured.

TABLE 3

|  | SPF |
| --- | --- |
| Example 1 | 19.2 |
| Example 2 | 23.5 |
| Comparative Example 1 | 11.6 |
| Comparative Example 2 | Cannot be Emulsified |
| Comparative Example 3 | Cannot be Emulsified |

As can be seen from Table 3 above, the SPF value of Example 1 is 7.6 higher than that of Comparative Example 1, and the SPF value of Example 2 is 11.9 higher than that of Comparative Example 1.

Therefore, the sunscreen composition according to the present invention can exhibit an excellent ultraviolet blocking effect by including cerium oxide surface-modified with a fatty acid, thereby allowing it to be used effectively as a composition for producing cosmetics for blocking ultraviolet rays.

Since the sunscreen composition according to an embodiment of the present invention exhibits a high kinematic viscosity in the low-frequency and high-frequency regions, the formulation has excellent emulsification/dispersion phase stability and excellent spreadability, and thus the sunscreen composition can be effectively used as a cosmetic composition for blocking ultraviolet rays.

Further, the sunscreen composition according to an embodiment of the present invention can absorb UVA1 of the mid-wavelength region of ultraviolet rays, thereby absorbing ultraviolet rays in the entire regions of UVA1 to UVA2, and it can have an excellent UV blocking effect due to a high sun protection factor (SPF).

In addition, the sunscreen composition according to an embodiment of the present invention has a low light refractive index of the particles, thereby preventing the white cast phenomenon in which a white color appears when applied to the skin, and thus the sunscreen composition can be used as a cosmetic composition for blocking ultraviolet rays which shows a natural color.

Further, since the sunscreen composition according to an embodiment of the present invention comprises cerium oxide particles that are surface-modified with the fatty acid, thus increasing emulsifiability into oil-in-water, water-in-water and non-aqueous formulations, the sunscreen composition can be used for preparing cosmetic compositions for blocking ultraviolet rays with various formulations.

What is claimed is:

1. A sunscreen composition comprising:
cerium oxide ($CeO^2$) particles surface-modified with a saturated fatty acid having 10 to 30 carbon atoms or an unsaturated fatty acid having 10 to 30 carbon atoms, wherein a kinematic viscosity of the sunscreen composition is 876 dPa·s at low frequency (0.1 Hz) and 10,200 dPa·s at high frequency (100 Hz), the saturated fatty acid having 10 to 30 carbon atoms is undecylic acid, tridecylic acid, myristic acid, palmitic acid, margaric acid, stearic acid, nonadecylic acid, arachidic acid, heneicosanoic acid, behenic acid, tricosanoic acid, lignoceric acid, pentacosanoic acid, cerotic acid, heptacosanoic acid, montanic acid, nonacosanoic acid or melissic acid, the unsaturated fatty acid having 10 to 30 carbon atoms has a ratio of the number of double bonds to carbon number of 18:1 to 18:3, and the sun protection factor (SPF) value of the sunscreen composition is equal to or higher than 19.2.

2. The sunscreen composition of claim 1, wherein the unsaturated fatty acid having 10 to 30 carbon atoms is palmitoleic acid, vaccenic acid, oleic acid or trans-elaidic acid.

3. The sunscreen composition of claim 1, wherein the content of the saturated fatty acid or the unsaturated fatty acid may be 0.3 to 15 wt %, 0.5 to 11 wt %, and 1 to 10 wt %, based on the surface-modified cerium oxide ($CeO_2$) particles.

4. The sunscreen composition of claim 1, wherein the cerium oxide ($CeO_2$) particles have a primary particle size of 10 to 30 nm, and have a secondary particle size of 100 to 500 nm, and a ratio of the secondary particle size to the primary particle size is 5 to 50.

5. The sunscreen composition of claim 1, wherein the content of the surface-modified cerium oxide particles is 1 to 50 wt %, based on the total sunscreen composition.

6. The sunscreen composition of claim 1, further comprising: one or more particles selected from the group consisting of titanium oxide particles and zinc oxide particles.

7. The sunscreen composition of claim 6, wherein the content of the titanium oxide is 1 to 25 wt %, based on the total sunscreen composition, and the content of the zinc oxide particles is 1 to 25 wt %, based on the total sunscreen composition.

8. A method for preparing a sunscreen composition, comprising:
adding and stirring cerium oxide into purified water to prepare a supernatant;
adding and stirring a saturated fatty acid having 10 to 30 carbon atoms or an unsaturated fatty acid having 10 to 30 carbon atoms into the supernatant;
drying the stirred solution to obtain cerium oxide particles surface-modified with the fatty acid;
dispersing the cerium oxide particles surface-modified with the fatty acid in an organic solvent; and
mixing the organic solvent with one or more substances selected from the group consisting of silicone oil, fibrous agents, emulsifiers, moisturizers, plasticizers, and purified water,
wherein a kinematic viscosity of the sunscreen composition is 876 dPa·s at low frequency (0.1 Hz) and 10,200 dPa·s at high frequency (100 Hz), the saturated fatty acid having 10 to 30 carbon atoms is, undecylic acid, tridecylic acid, myristic acid, palmitic acid, margaric acid, stearic acid, nonadecylic acid, arachidic acid, heneicosanoic acid, behenic acid, tricosanoic acid, lignoceric acid, pentacosanoic acid, cerotic acid, heptacosanoic acid, montanic acid, nonacosanoic acid or melissic acid, the unsaturated fatty acid having 10 to 30 carbon atoms has a ratio of the number of double bonds to carbon number of 18:1 to 18:3, and the sun protection factor (SPF) value of the sunscreen composition is equal to or higher than 19.2.

* * * * *